United States Patent
Hong et al.

(10) Patent No.: US 6,827,950 B2
(45) Date of Patent: Dec. 7, 2004

(54) PHARMACEUTICAL COMPOSITION COMPRISING ARALIA EXTRACTS

(75) Inventors: Eun-Kyung Hong, Seoul (KR); Young-Shin Chung, Seoul (KR); Yeong-Bok Han, deceased, late of Seoul (KR); by Yong-woo Han, legal representative, Seoul (KR); Yun Hui Choi, Kyoungki-do (KR); Seong-Jin Kim, Seoul (KR); Hae-Ri Kim, Seoul (KR); Bu-Hyeon Kang, Seoul (KR)

(73) Assignee: Medvill Co., Ltd., Seoul (KR)

( * ) Notice: Subject to any disclaimer, the term of this patent is extended or adjusted under 35 U.S.C. 154(b) by 0 days.

(21) Appl. No.: 10/219,613

(22) Filed: Aug. 15, 2002

(65) Prior Publication Data

US 2004/0033274 A1 Feb. 19, 2004

(51) Int. Cl.$^7$ ............................................. A61K 35/78
(52) U.S. Cl. ..................................................... 424/725
(58) Field of Search ............................... 424/195.1, 725

(56) References Cited

FOREIGN PATENT DOCUMENTS

| JP | 408099993 A | * | 4/1996 |
| KR | 2001076920 A | * | 8/2001 |

OTHER PUBLICATIONS

Head, Kathleen, ND, "Natural Therapies for Ocular Disorders Part Two: Cataracts and Glaucoma," Alternative Medicine Review, vol. 6, No. 2, (2001) p. 141.

Ross, W. M., Creighton, M. O., Trevithick, J. R., Stewart –DeHaan, P. J., and Sanwal, M., "Modelling Cortical Cataractogenesis: VI. Induction by Glucose in vitro or in Diabetic Rats: Prevention and Reversal by Glutathione," Exp. Eye Res. (1983), 37, 559–573.

Varma, Shambhu D., and Kinoshita, Jin H., "Inhibition of Lens Aldose Reductase By Flavonoids—Their Possible Role in the Prevention of Diabetic Cataracts," Biochemical Pharmacology, vol. 25, pp. 2505–2513, Pergamon Press, 1976, Printed in Great Britain.

Nakai, N., Fujii, Y., Kobashi, K., and Nomura, K., "Aldose Reductase Inhibitors: Flavanoids, Alkaloids, Acetophenones, Benzophenones, and Spirohydantoins of Chroman," Archives of Biochemistry and Biophysics, vol. 239, No. 2, Jun., pp. 491–496, 1985.

Varma, S.D., Mikuni, I., Kinoshita, J.H., "Flavonoids as Inhibitors of Lens Aldose Reductase," Science, vol. 1888, pp. 1215–1216, Feb. 12, 1975.

Varma, S.D., Mizuno, J.H., and Kinoshita, J.H., "Diabetic Cataracts and Flavonoids," Science, vol. 195, pp.. 205–206, Jan. 14, 1977.

Altomare, E., Grattagliano, I., NVendemaile, G., Micelli-–Ferrari, T., Signorile, A., and Cardia, L., "Oxidative protein damage in human diabetic eye: evidence of a retinal participation," European Journal of Clinical Investigation (1997) 27, 141–147.

* cited by examiner

Primary Examiner—Patricia Leith
(74) Attorney, Agent, or Firm—Jeffrey L. Costellia; Nixon Peabody LLP

(57) ABSTRACT

The present invention relates to Aralia extracts and a therapeutic agent comprising Aralia extracts as an active ingredient. The composition and therapeutic agent according to the present invention are effective in preventing cataract, delaying the development of cataract, and treating cataract. According to the present invention, extracts of Aralia are obtained by extraction with alcohol. Addition of myo-inositol or taurine to the extracts will result in a synergistic effect in the treatment of cataract. In addition, oral administration of beverages, galenicals, and nutraceuticals, which comprise Aralia extracts as an active ingredient, will be effective in prevention, delay and treatment of cataract caused by complications of diabetes. Aralia extracts will have the same effect in the case where they are used as an ophthalmic agent. They can also be used as an eye drop or an eye ointment.

12 Claims, 13 Drawing Sheets

0hr

<degree 0>

9hr

<degree 1>

14hr

<degree 2>

19hr

<degree 3>

24hr

<degree 4>

48hr

<degree 5>

▲ CHCl₃ (AC); ☐ BuOH (AB); ● EtAc (AE); ■ Water (AW); ○ Control.

● : 24 hours AC pre-incubation
△ : 48 hours AC pre-incubation
○ : without AC pre-incubation ○ : 24 hours prior incubation with 20mM xylose
● : 48 hours prior incubation with 20mM xylose □ : AC treated xylose media
■ : myo-inositol, taurine and AC treated xylose media
○ : M199 control media without xylose □ : AC treated xylose media
■ : myo-inositol, taurine and AC treated xylose media
○ : M199 control media without xylose

PHARMACEUTICAL COMPOSITION COMPRISING ARALIA EXTRACTS

BACKGROUND OF THE INVENTION

1. Field of the Invention

The present invention relates to a composition comprising Aralia extracts for the prevention and treatment of cataract. In particular, the present invention relates to a composition for prevention or treatment of cataract comprising solvent extracts of Aralia, wherein said solvent is ethanol, methanol or a mixture thereof. Also, the present invention relates to a process for preparing a composition for prevention and treatment of cataract, wherein the process comprises the following steps of: a) extracting Aralia with alcohol; b) filtrating the extract obtained from step a) to give a residue and a filtrate; and c) removing the alcohol from the filtrate obtained from step b) to give a powder.

2. Description of the Prior Art

Cataract is a disease caused by the degeneration of lenses due to aging. Although this disease may occur naturally, the frequency of occurrence is highest in diabetic patients with complications.

According to a survey performed by the National Statistical Office of Korea on the leading causes of death in 1991, diabetes ranked $6^{th}$, accounting for 2.8% of all deaths in Korea (National Statistical Office, 1992). Diabetes often leads to fatality due to complications resulting from high blood glucose levels. A high level of blood glucose exposure in the body for 15 to 20 years damages several organs due to the disturbance in energy metabolism. Thus, chronic diabetic complications, such as diabetic cataract, diabetic nephropathy, diabetic peripheral nerve disorder, diabetic hyperlipemia, etc., often occur. (Vlassara H. (1990), Chronic diabetic complications and tissue glycosylation, *Diabetes Care* 13(11): 1180-1185) Patients with diabetes have a 25 times higher risk of blindness, 20 times higher risk of kidney failure, and 2-6 times higher risk of coronary cardiac disorders, in comparison with a normal person.

Cataract is a major cause of blindness, since approximately 35% of all cases of blindness are caused by cataract. (Chylack L. T. (1984), Mechanism of Senile Cataract Formation, *Ophtalmol.* 91: 596-602) Cataract is found in more than 50% of people in their sixties, more than 60% of people in their seventies, and more than 70% of people in their eighties. Patients with diabetes often develop cataract in their forties or fifties. Thus, vision is deteriorated and weakened at a high rate. In particular, cataract may occur in those patients who are in their twenties or thirties when they have insulin-dependent diabetes. Cataract is a visual disorder that is caused when light cannot reach the retina due to cloudiness of the lens. This disease can be treated by implanting an artificial lens through surgery. However, after surgery, patients' eyes may be inflamed, or healing of the wound may be delayed due to diabetes. In addition, patients are more apt to bleed. Especially, there are many cases where cataract caused by insulin-dependent diabetes progresses to after-cataract, which mean that vision regained after surgery is lost again. (In addition, patients are more apt to bleed, and the vision regained by surgery might be lost again.)

Existing aldose reductase inhibitors that were developed as a therapeutic agent for diabetic complications are not currently in use because of their side effects. Recently, in an attempt to develop medicines that overcome such side effects and are more effective, research for the synthesis of an aldose reductase inhibitor has been performed by further looking into the relationship between the structure and the activity of the aldose reductase inhibitor and determining the characteristical structure that has higher activity and can function continuously. (Potier N., Barth P., Tritsch D., Biellmann J.-F. and Van Dorsselaer A. (1997), Study of non-covalent enzyme inhibitor complexes of aldose reductase by electrospray mass spectrometry, *Eur. J Biochem.* 243: 274-282).

There have been active research activities for effective aldose reductase inhibition using flavonoid components that are extracted from the root of *Scutelladose reductaseia baicalensis*. Many anti-oxidant materials, such as vitamin C, vitamin E, glutathione, catalin, baineiting, catachrome-OFTAN, Vita-iodurol, quinax, etc., are currently known as medicines for cataract. (Chasovnikova L. V., Formazyuk V. E., Sergienko V. I., Boldrev A. A., and Severin S. E. (1990), The antioxidative properties of carnosine and other drugs. *Biochem. International* 20(6): 1097-1103).

Catalin is also used as a therapeutic agent for cataract. However, such medication cannot cure the degenerated lens protein completely. Thus, catalin is not actually valuable. Currently, the treatment for cataract depends on surgery.

In order to prevent diabetes or to prevent and treat complications, Korean Patent Publication No. 10-195886 discloses a formulation for lowering blood glucose levels of diabetic patients and lowers blood lipid concentrations using galenical substances, including *Cordyceps sinensis*, cow bezoar, Phellodendri Cortex, etc.

SUMMARY OF THE INVENTION

Accordingly, the object of the present invention is to provide Aralia extracts that are effective for preventing, delaying or treating cataract caused by high blood glucose levels.

Another object of the present invention is to provide a composition comprising another active ingredient, in addition to the Aralia extracts.

These objects of the present invention can be achieved by solvent extracts from Aralia.

The present invention provides a composition for prevention or treatment of cataract comprising solvent extracts of Aralia, wherein said solvent is ethanol, methanol or a mixture thereof.

Further, the present invention provides a process for preparing a composition for prevention and treatment of cataract, wherein the process comprises the following steps of:

a) extracting Aralia with alcohol;
b) filtrating the extract obtained from step a) to give a residue and a filtrate; and
c) removing the alcohol from the filtrate obtained from step b) to give a powder.

BRIEF DESCRIPTION OF THE DRAWINGS

The above objects, other features and advantages of the present invention will become more apparent by the preferred embodiments described with reference to the accompanying drawings, in which.

DETAILED DESCRIPTION OF THE PREFERRED EMBODIMENTS

The lens of the eye is the only part of the body that is transparent and comprises about 35% protein and about 63% water. Unlike other organs, the lens lacks blood vessels and metabolizes protein very slowly. Once protein damage occurs in the lens of the eye, it is difficult to recover from such damage. Such protein damage can be caused by the aging. The lens is supplied with nutrition from the aqueous humor that is connected to blood vessels. Therefore, the lens of the eye is indirectly affected by blood.

The most widely known mechanism of cataract caused by diabetes is the activation of polyol pathway and oxidative stress. (Beyer T. A. and Hutson N. J. (1986), Introduction: Evidence for the role of the polyol pathway in the pathophysiology of diabetic complications, *Metabolism* 35(4): 1-3)

The polyol pathway in the lens has been well known as a key to understanding the osmotic pressure change that causes cataract, since the accumulation of sorbitol had been observed in the lens of diabetic mice. (Chylack L. T. and Kinoshita J. H. (1969), A biochemical evaluation of a cataract induced in a high-glucose medium, *Invest. Ophthalmol.* 8: 401-406) Once blood glucose levels increase, glucose concentration in the aqueous humor rapidly increases to 90% blood glucose level. Glucose in the aqueous humor is more rapidly absorbed into the lens by facilitated transportation, rather than by diffusion. It is known that there is no need of insulin when absorbed by facilitated transportation. Glucose flown into the lens is metabolized to polyol by hexokinase (HK) or aldose reductase, which is an enzyme in the rate limiting step.

Figure 1:
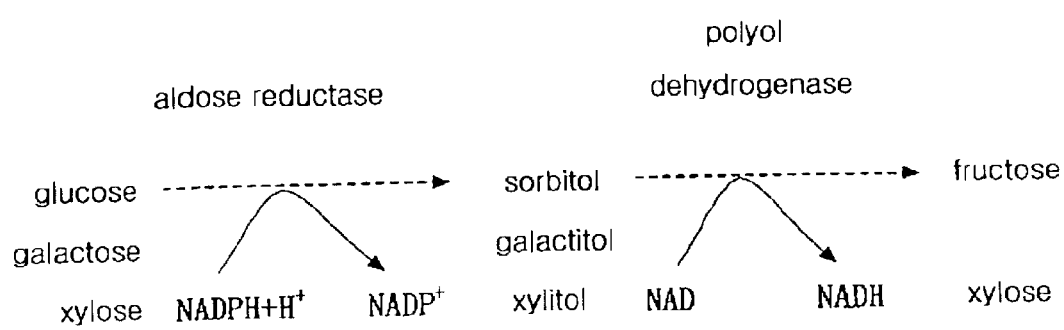
FIG. 1 is a schematic drawing of a polyol pathway.

Such a polyol pathway is not activated under normal physiological conditions. However the increase in the activity of aldose reductase and the decrease in the activity of sorbitol dehydrogenase in diabetes patients cause the activation of the polyol (sorbitol) pathway (FIG. 1).

While aldose reductase induces the reduction of glucose alcohol or aldehyde, polyol dehydrogenase characteristically reacts with polyols. Thus, polyols that are not further metabolized are accumulated in the cells. Since polyols have a property of polarity, they cannot pass through the cell membrane, and thus are accumulated in the cells. The accumulated polyols cause osmotic damage. Continuous expansion and destruction of the fiber tissue in the lens lead to the formation of a visible vacuole. If formation of the visible vacuole is increased, the lens becomes cloudy. Such cloudiness causes cataract.

The progress of the cataract due to diabetes is also associated with oxidative stress. If the polyol pathway increases, consumption of NADPH also increases. Accordingly, NADPH that is required in converting oxidated glutathione (GSSG) into reduction type (GSH) will be insufficient. Insufficiency of GSH that reduces $H_2O_2$ into $H_2O$ will result in the increase of the formation of the hydroxyl radical. Thus, formation of a cataract is a result of the disturbance in control of osmotic pressure and oxidative stress complicated from the diabetes.

Aldose reductase inhibitors that inhibit the production of polyols (sorbitol) on the polyol pathway are effective in preventing, alleviating or curing cataract caused by blood glucose. Quercetin, quercitrin, sorbinil, AL1576, TMG, statil, tolrestat, aporphine type, benzylisoquinoline type, berberine type, etc., are all known to be aldose reductase inhibitors. However, many of these compounds are suspected to be carcinogenic and exhibit side effects such as nausea. In addition, it has been reported that adverse side effects occur in human organs, such as the liver.

On the basis of the development and progress of cataract due to high blood glucose levels, the inventors of the present invention found the fact that Aralia extracts are effective in preventing and treating cataract caused by glucose, since the Aralia extracts function well as an aldose reductase inhibitor in the polyol pathway and relieve oxidative stress.

Aralia elata grows naturally in East Asia. The peel in Aralia contains several kinds of triterpenoids including saponin. In the bark, several glycosides, such as elatoside E, elatoside F, oleanolic acid glycoside, etc., which are effective in lowering blood glucose levels, and elatoside A and elatoside B, which inhibit absorption of ethanol, exist. (Yoshikawa M., Harada E., Matsuda H., Murakami T., Yamahara J. and Murakami N. (1993), Elatosides A and B, potent inhibitors of ethanol absorption in rats from the bark of Aralia elata. See the Structure-activity relationships of oleanolic acid oligoglycosides. *Chem. Pharm. Bull.* (Tokyo) 41: 2069-2071) Oleanolic acid, which is a type of saponin, prevents the liver from being damaged by several kinds of chemical materials.

The present inventors used Aralia extracts in the lens of a rat that has a cataract, and found that the degree of cloudiness was lowered. To obtain Aralia extracts, solvents such as ethanol, methanol or a mixture thereof can be used. The ethanol or methanol extracts may be further extracted by using ethyl acetate, chloroform, butanol, etc.

Aralia extracts in the present invention can be used alone. Alternatively, Aralia extracts may be used in combination with either one or both of myo-inositol and taurine.

The present invention can be used in the preparation of a galenical, an ophthalmic solution, a nutraceutical, and a beverage, all of which comprise Aralia extracts as an active ingredient. Aralia extracts in the effective amount for treatment are administered alone or in a form that contains a pharmaceutically acceptable carrier, excipient or diluent, through subcutaneous, oral or intramuscular administration. Aralia extracts are also administered in various forms, such as an eye ointment or other forms that have been known to be proper in the art. As an oral dosage form suitable for the extracts of the present invention, forms of preparation, such as a tablet, a capsule, a solution, a suspension, syrup or beverage, etc., are used. A preparation that contains Aralia extracts for parenteral administration can be formulated in the form of a sterilized injection (such as a sterilized liquid that can be injected or an oily suspension), an eye drop, an eye ointment, etc. The suspension is prepared by the use of a suitable dispersing agent, a wetting agent or a suspending agent according to the process that is well known in the art to which the present invention pertains.

Aralia extracts of the present invention can be used as a beverage that contains water, a sweetener and a suitable additive. This beverage can additionally contain either one or both of myo-inositol and taurine. Since Aralia itself has been used as food, no toxicity is found in its extracts. Therefore, Aralia extracts provided in the form of a beverage that additionally contains a suitable sweetener and a preservative can be taken at any time by diabetic patients. Beverages that contain Aralia extracts will be helpful in preventing and treating cataract.

When Aralia extracts according to the present invention are used as galenicals, the dose may vary depending on the degree of seriousness of a disease, patient's gender, age and weight, and the desired effect. Generally, upon oral administration into an adult, 20–70 mg, of Aralia extracts can be administered per 1 kg of the patient's weight. Upon injection, 5-30 mg of Aralia extracts can be administered when the patient weighs 60 kg.

Although the present invention is further described in the examples below, the scope of the present invention is not limited to that described in these examples.

EXAMPLE 1

Preparation of Aralia Extracts 1.2 L of 80% ethanol was added to 200 g of the ground branches of Aralia elata. Extraction was processed for 48 to 72 hours at room temperature while stirring at intervals. Eluent was poured out, and same amount of 80% ethanol was added again to the residue and the same process was repeated for re-extraction.

After mixing the second eluent with the first eluent, ethanol was distilled off by a rotary evaporator. The remaining eluent was freeze-dried to give a powder. As a result, a brown-colored powder was obtained in 14% yield.

Figure 2:
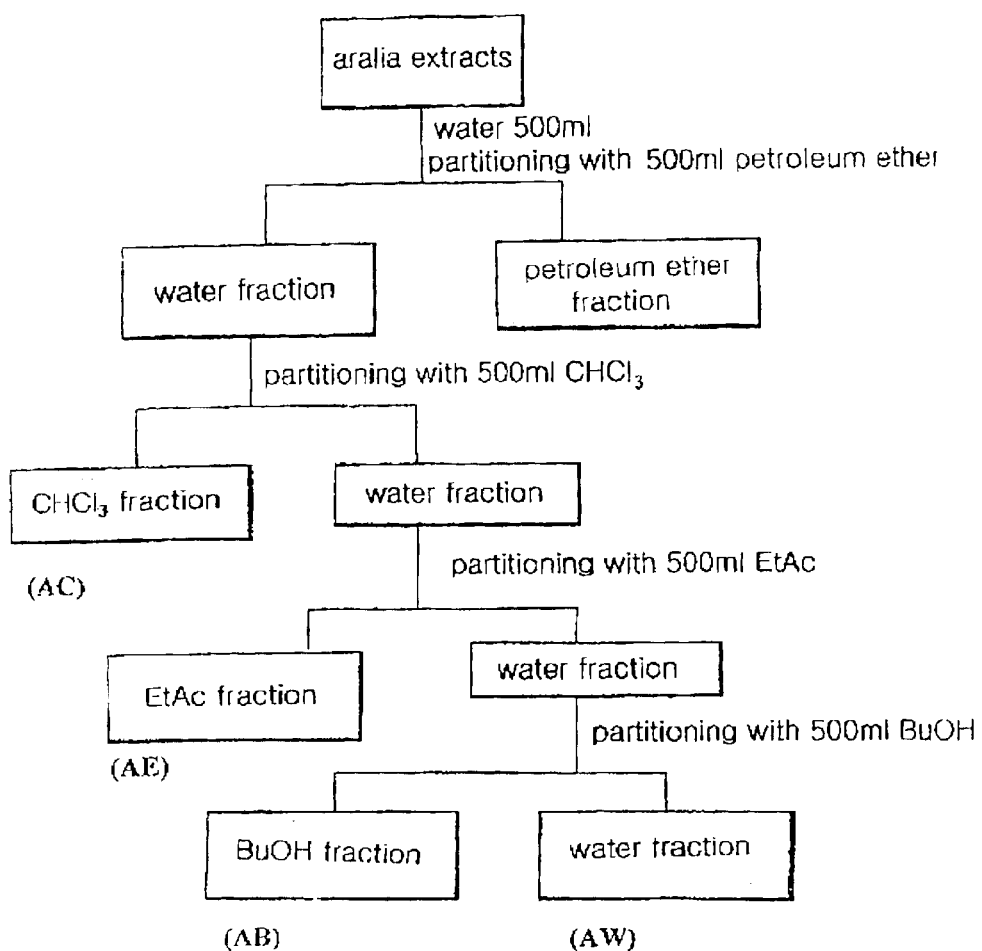
FIG. 2 is a schematic drawing of the step of separating fractions from Aralia according to the present invention.

An ethanol extract was divided into a chloroform layer, an ethyl acetate layer, a butanol layer, and a water layer by solvent extraction as shown in FIG. 2. According to the extraction method of FIG. 2, 160 g of Aralia extract was dissolved in 500 mL of water and then extracted twice with 250 mL of petroleum ether each. The petroleum ether layers were separated off and then the remaining water layer was extracted again with 500 mL of chloroform to give a chloroform layer from which 4.92 g (3.04%) of sticky substances were obtained. The remaining water layer was extracted with 500 mL of ethyl acetate to give an ethyl acetate layer from which 4.10 g (2.54%) of solid substances were obtained. Thereafter, the remaining water layer was extracted with 500 mL of butanol to give a butanol layer from which 29.39 g (18.2%) of solid substances were obtained, and a water layer from which 107.87 g (66.8%) of solid substances were obtained

EXAMPLE 2

Formulation of Aralia Extracts a. Tablet 250 mg of freeze-dried extract powder of the present invention prepared in Example 1 was mixed with 260 mg of lactose as an excipient for direct tableting, 35 mg of avicel (microcrystalline cellulose), 15 mg of sodium starch glyconate as a disintegration adjuvant, and 80 mg of tableting low-hydroxypropylcellulose (L-HPC) in a U-shaped mixer for 20 min. 10 mg of magnesium stearate was then further added and mixed for 3 min. Through a quantitative test and a constant humidity test, the mixture was then tableted and film-coated to obtain tablets each containing 250 mg of the extract.

b. Syrup

With a defined amount of white glucose dissolved in a defined amount of water, 80 mg of paraoxymethyl benzoate and 16 mg of paraoxypropyl benzoate were added as preservatives. Then, 4.5 g of the freeze-dried, extract powder of the present invention prepared in Example 1 was added and completely dissolved in the glucose solution at 60° C. The resulting solution was then cooled and diluted with distilled water to be 150 ml in volume, thus obtaining 3% syrup.

c. Capsule 300 mg of powdered extract of the present invention prepared in Example 1 was mixed with 200 mg of lactose as a carrier. Hard gelatin capsules were then packed with the resulting mixture to obtain the present invention capsules.

d. Beverage 500 mg of extract powder of the present invention prepared in Example 1 was dissolved in an appropriate amount of water. Then, there were added vitamin C as a supplemental component, citric acid, sodium citrate and high fructose syrup as corrigents, and sodium benzoate as a preservative. The resulting solution was diluted with water to be 100 ml in volume, thus obtaining a 0.5% composition for beverage.

e. Injection 200 mg of freeze-dried, mixed extract powder of the present invention prepared in Example 1 was dissolved by heating it in 200 mg of physiological saline containing 1% polyoxyethylene-hydrogenized castro oil. An injection containing the extracts in the concentration of 0.1% was prepared.

f. Eye Drop Solution 50 mg of freeze-dried, extract powder of the present invention prepared in Example 1 was dissolved in a non-aqueous injection solvent, such as sterile purified water, ethanol, PEG, etc. This solution was completely dissolved by adding a disintegration-aiding agent, such as sodium benzoate. By adding a stabilizing agent used in an injection or a preservative, 2–5% of the solution was prepared.

EXAMPLE 3

Solvent Extract of Aralia Inhibiting Activity of Aldose Reductase

An enzymogen of aldose reductase was prepared according to the Hayman method. (Hayman S. and Kinoshita J. H. (1965), Isolation and Properties of Lens Aldose Reductase. *J. Biol. Chem.* 240(5); 877-882) After homogenization with the addition of 100 mM of potassium phosphate buffer (pH 7.0) that corresponds to 10 times by volume of wet weight of the lens of white rats, the homogeneous liquid was centrifuged for 20 minutes at 4° C. at 10,000 rpm. The supernatant obtained by centrifugation was used as an enzymogen.

Activity of aldose reductase was measured by the Das method. (Das B. and Srivastava S. K. (1985) Purification and Properties of Aldose Reductase and Aldehyde Reductase II from Human Erythrocyte. *Anal. Biochem. Biophys.* 238 (2); 670-677) An enzymogen prepared by above method, 10 mM DL-glyceraldehyde and 0.16 mM NADPH were dissolved in 0.1M of phosphate buffer (pH 6.2). At 340 nm, the optical density (O.D.) was measured for 5 minutes at intervals of 1 minute. By calculating the difference of O.D. for five minutes, the percentage of absorbance for the control group was indicated as an enzyme inhibition rate of the extracts. By plotting the rate of enzyme inhibition (%) to the concentration of extracts (log value), 50% enzyme inhibition concentration was obtained.

An experiment was performed using Aralia fractions extracted with chloroform (AC), ethyl acetate (AE), butanol (AB), and water (AW). In Table 1, the inhibition effects of fractions on the activity of aldose reductase was represented as $IC_{50}$ (a concentration that inhibits 50% activity). As a result of the experiment, the function of the chloroform extract, ethyl acetate extract, water extract, and butanol extract in inhibition activity was higher in the order named.

TABLE 1

Inhibitory effects of Aralia extracts on the activity of Aldose Reductase

| Extracts | $IC_{50}$ (μg/ml) |
|---|---|
| Chloroform (AC) | 2.11 |
| Ethyl acetate (AE) | 5.92 |
| Butanol (AB) | 27.2 |
| Water (AW) | 16.9 |

EXAMPLE 4

Anti-Oxidative Activity of Aralia Extracts

Figure 3:
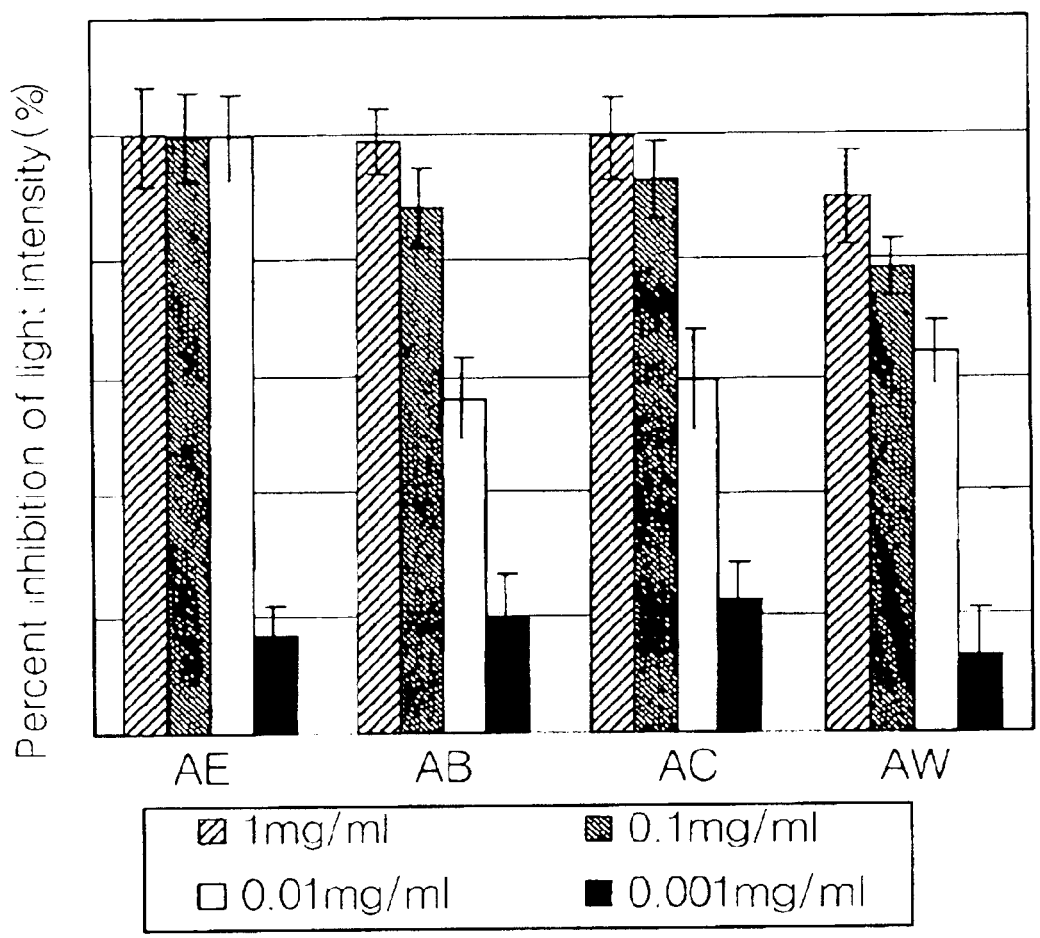
FIG. 3 is a graph showing anti-oxidation activity of each extract by a CL analysis performed with ABEI-microperoxidase.

Anti-oxidative activity of Aralia extracts was measured by using chemiluminescence (CL). (Birks J. W. (1989), Chemiluminescence and Photochemical Reaction Detection in & Chromatography, VCH Publisher: 10-13) 200 ul of 0.6 uM ABEI and 200 ul of extracts were added in a polystyrene tube. 35% hydroperoxide and 10 mg/ml of microperoxidase were diluted in the ratio of 1:100 and automatically injected into a luminometer. Light intensity according to chemical reaction was measured for 2 seconds by the luminometer (LB 9502, Clilumat, Germany). Anti-oxidation function of extracts is indicated by inhibition percentage (%) of light intensity upon reaction. As a result (see FIG. 3), CL inhibition function of the AE fraction was 95% or more, at 0.01 mg/ml. Thus, the AE fraction was the best of the four fractions. The AC fraction and the AB fraction exhibit similar anti-oxidation functions. The AW fraction exhibits the less effective on anti-oxidative activity.

EXAMPLE 5

Figure 4:
FIG. 4 shows photographs of lenses having different degrees of cloudiness induced by 20 mM of xylose.
Figure 4:
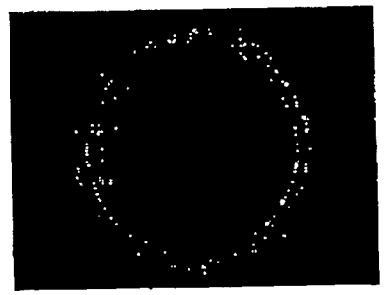
Figure 4:
Figure 4:
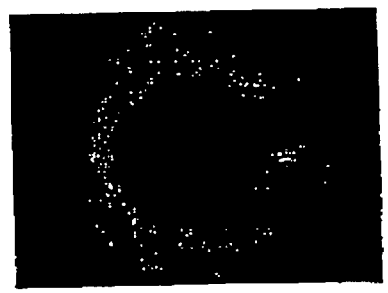
Figure 4:
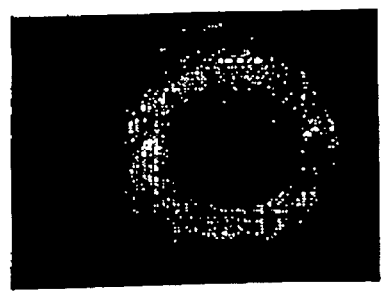
Figure 4:

Effectiveness of Four Fractions of Aralia Extracts on the Delayed Generation of Cataract Caused by Glucose SD-rats (180–200 g) were sacrificed with $CO_2$ in which their eyes were removed. The eyes were preserved in an iodic solution for disinfection. The excised lens were placed on an M199 culture medium. After 24 hrs incubation, the protein concentractions were measured in the media. Lenses in the media containing low protein representing no scar on their surface were selected for further experiment. When the selected lenses were incubated in media containing 20 mM of xylose, cataract occured within 24 hours. The degree of cataract was indicated in an optional unit per pixel by obtaining the values of cloudiness of the lenses through an image analyzer. By examination through a microscope, the degree of cataract was classified into 0 to 5 for comparison (see FIG. 4).

Figure 5:
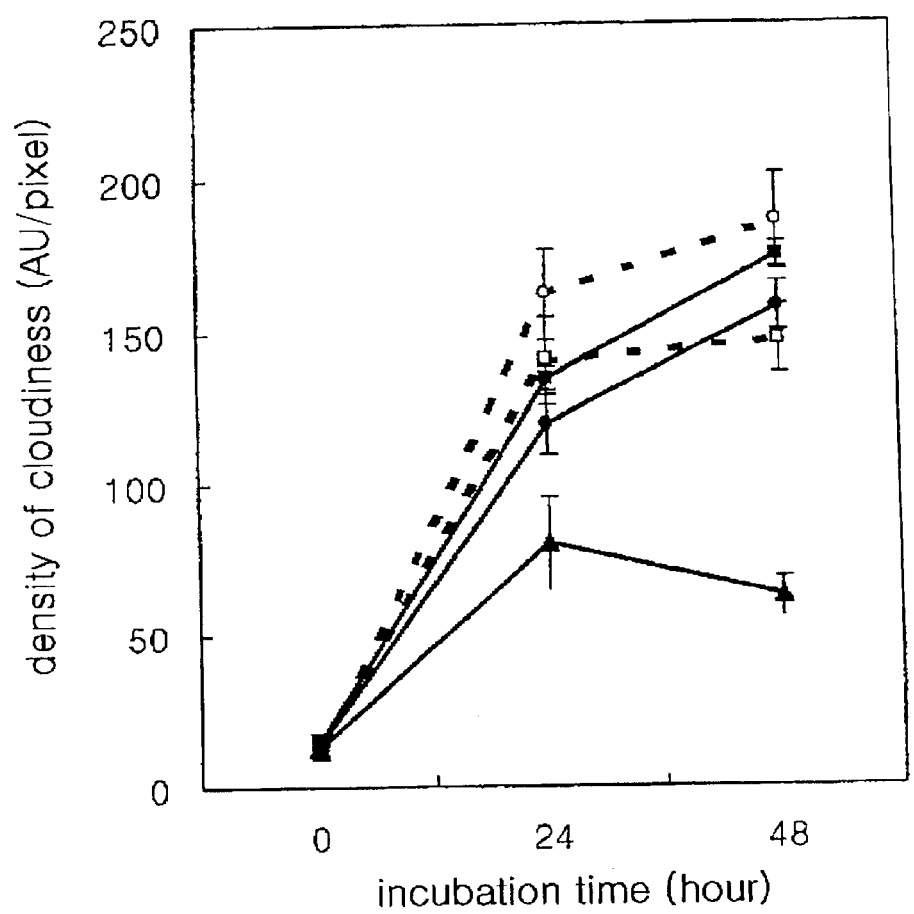
FIG. 5 is a graph showing cloudiness of lenses after the lenses are treated by each fraction.

FIG. 5 shows the effects of each extract on the cataract formation. Lenses were incubated with 20 mM xylose media(—O—), water fraction-treated xylose media (—■ —), ethyl acetate fraction-treated xylose media(—●—), butanol fraction-treated xylose media(—□—) and chloroform fraction-treated xylose media(—▼—) for 48 hours. The cloudiness of lenses was measured using the image analyzer and represented by arbitrary unit per pixel. Values are based on four or more experiments with 4-5 lenses and expressed as the mean±S.D. As a result, when four fractions were added at the concentration of 1 mg/ml, the AC fraction was most effective in significantly delaying the generation of cataract ($P<0.05$).

When the classic method (grading method in above, FIG. 4) was employed for estimation of the cloudiness, the following results were obtained. 90% of the lenses treated with AC fraction for 24 hours marked the grade 2 in cataract formation, while 10% showed the grade 1. After 48 hours, 75% graded 1 and 25% graded 2.

EXAMPLE 6

Effects of Chloroform (AC) Fraction in the Prevention of the Generation and Treatment of Cataract Experiment was performed to determine whether chloroform extract can prevent the generation of cataract, or result in recovery from cataract.

Figure 6:
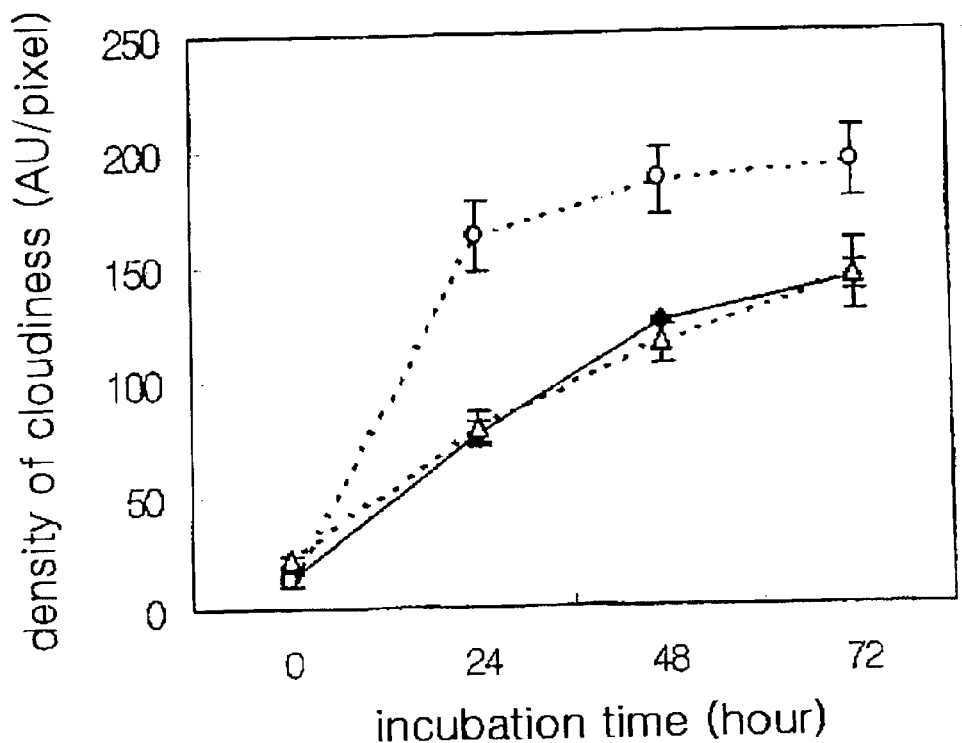
FIG. 6 is a graph showing the influence of an AC fraction on the prevention of cataract.

The effect of the AC fraction on the prevention of the generation of cataract caused by glucose is shown in FIG. 6. A controlled culture medium containing the AC fraction was used for the pre-incubation of lenses for 24 (—●—) or 48 hours(—▲—). After replacing the control culture medium with a xylose-added culture medium, cataract was induced for 72 hours. Values are based on three or more experiments with 4-5 lenses and expressed as mean±S.D. As a result, the prominent preventive effects of AC fraction was observed in lenses with pre-incubation for 24 hours or 48 hours, compared with control(—O—). There was little difference in the preventive effects between the conditions of 24 hours pre-incubation and 48 hours. Conclusively, pre-incubation with the AC fraction significantly inhibited the generation of cataract induced for 72 hours in culture media.

Figure 7:
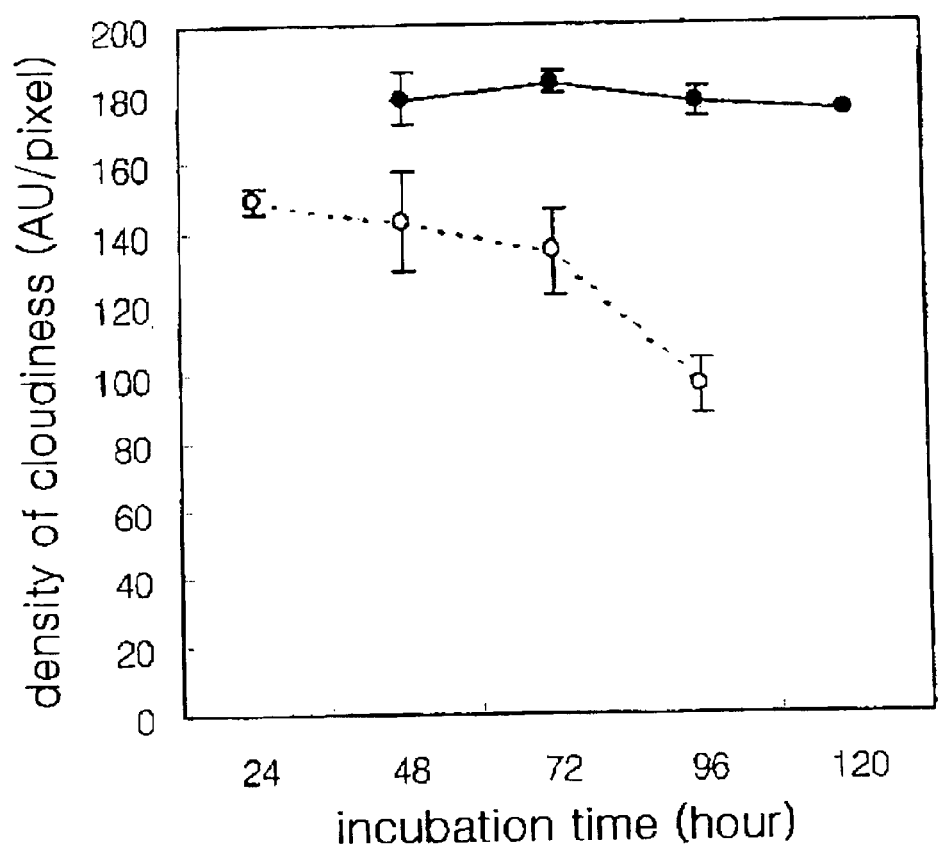
FIG. 7 is a graph showing the influence of an AC fraction on the recovery from cataract.

In order to demonstrate the recovery function of AC fraction against cataract that were already generated with glucose, lenses were treated with the AC fraction for 72 hours after the incubation in 20 mM xylose media for 24 hours(—O—) or 48 hours(—●—). Changes of the cloudiness during the treatment were measured and shown in FIG. 7. Values are based on three or more experiments with 4-5 lenses and expressed as the mean±S.D. Upon the treatment of the AC fraction after 24 hours of induction of cataract, no significant difference was shown in the cloudiness for up to two days. On the third day, however, the degree of cloudiness was significantly reduced. Cloudiness was reduced by 35.7% on the third day when compared with cloudiness measured before the treatment of the AC fraction. The reduction achieved on the third day was an approximately 80% total reduction achieved during the 3 days. When the treatment was started after 48 hours of cataract induction, there was a slight amount of reduction (approximately 2.4%). However, it was not significant. Rather, the degree of cloudiness increased on the first day of the treatment.

EXAMPLE 7

Effectiveness of Chloroform Extract on Oxidative Stress

Figure 8:
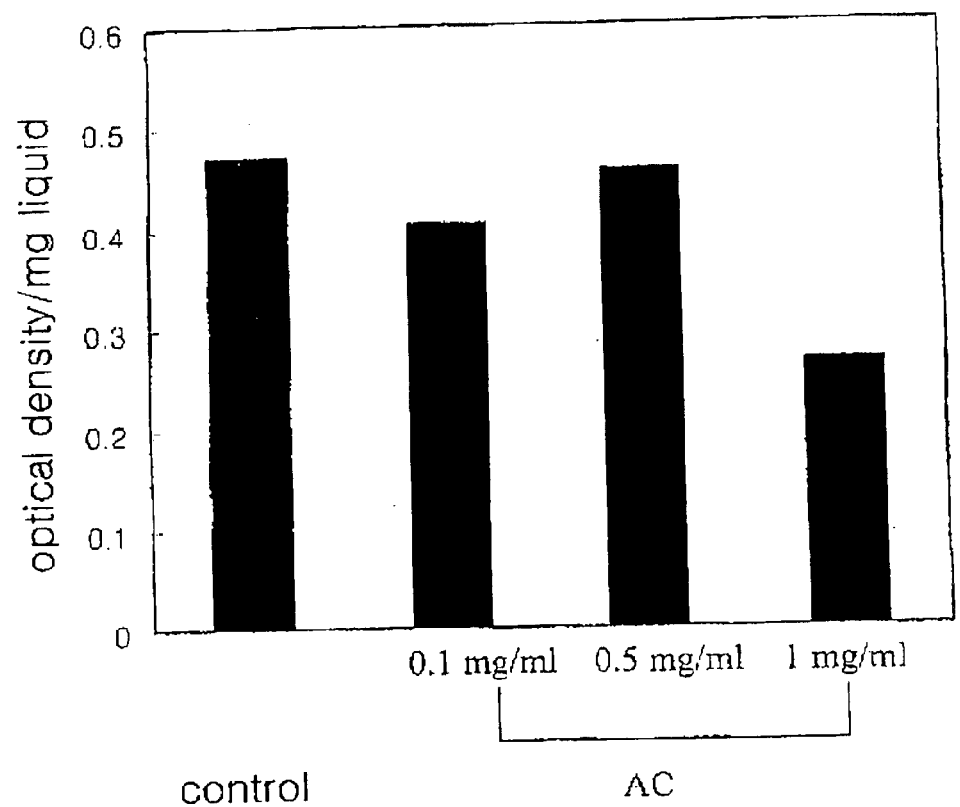
FIG. 8 is a graph showing the influence of an AC fraction on the formation of conjugates.

Oxidative stress was examined by measuring the amount of conjugate diene, which is a lipoperoxide. The mixture of chloroform and methanol and the homogeneous lens liquid were mixed and then centrifuged. Then, chloroform layer in the bottom was separated, dried under nitrogen gas, and treated with cyclohexane. The absorbance was measured at 233 nm. FIG. 8 shows the content of conjugate diene in the lenses treated with/without AC fraction for 48 hours in the 20 mM xylose culture media. 'Control' means that lenses were incubated with 20 mM xylose-treated media and 'AC' means that lenses were incubated with AC-treated xylose media. Each bar represents an average of four experiments with 4–5 lenses in each group. The amount of conjugated diene was significantly lowered by the treatment with 1 mg/ml of the AC fraction. Therefore, the AC fraction is believed to be effective on the inhibition of the conjugated diene production, which is the initial process of lipoperoxidation in the lenses.

EXAMPLE 8

Effectiveness on Cataract Due To Addition of Myo-inositol and Taurine to a Chloroform Extract of Aralia As a result of the previous experiment, the lower levels of myo-inositol and taurine were observed in lenses with cataract. Thus, it was examined whether the addition of myo-inositol and taurine to Aralia extracts synergistically increases their efficacy or not.

Figure 9:
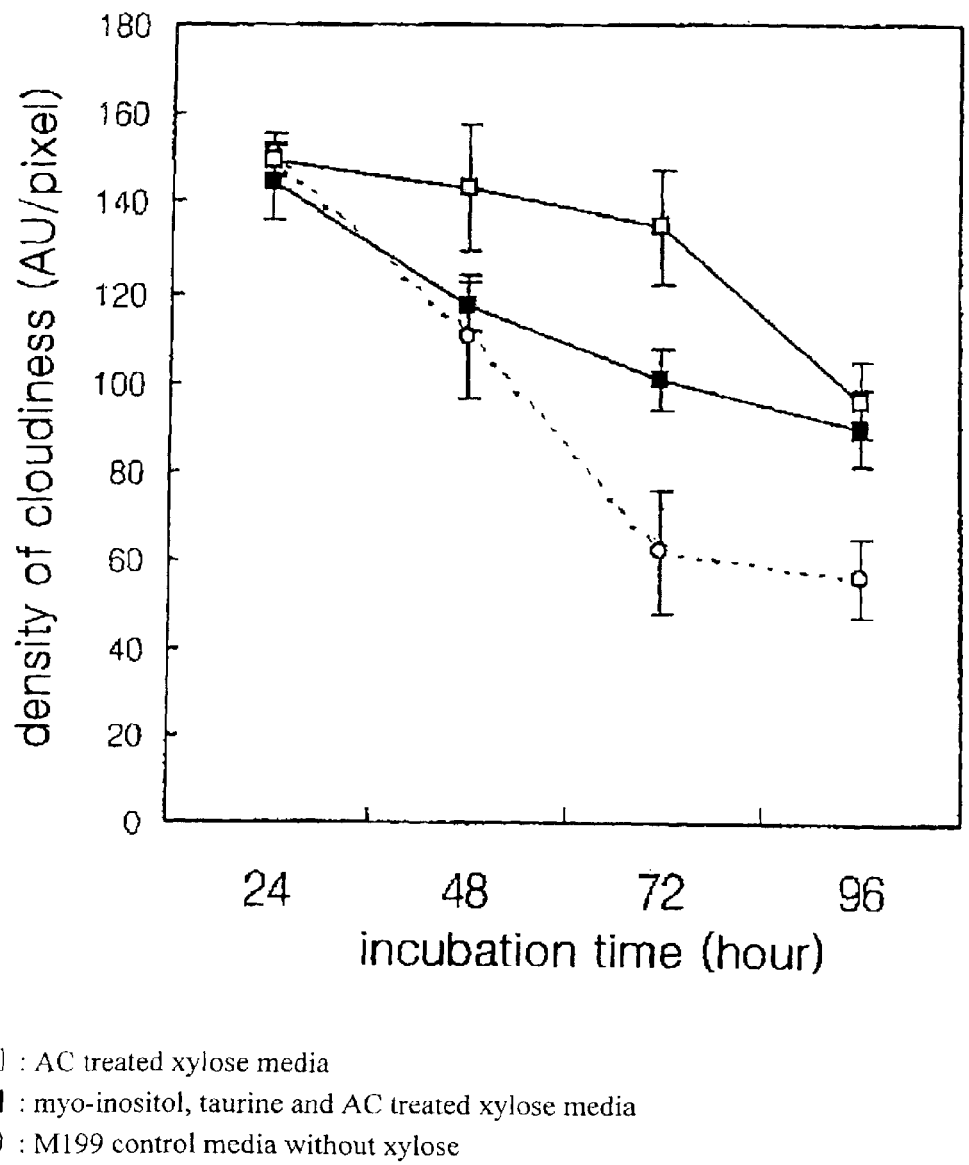
FIGS. 9 and 10 are graphs showing the influence of the addition of an AC fraction, and myo-inositol and taurine on the recovery from cataract.
Figure 10:
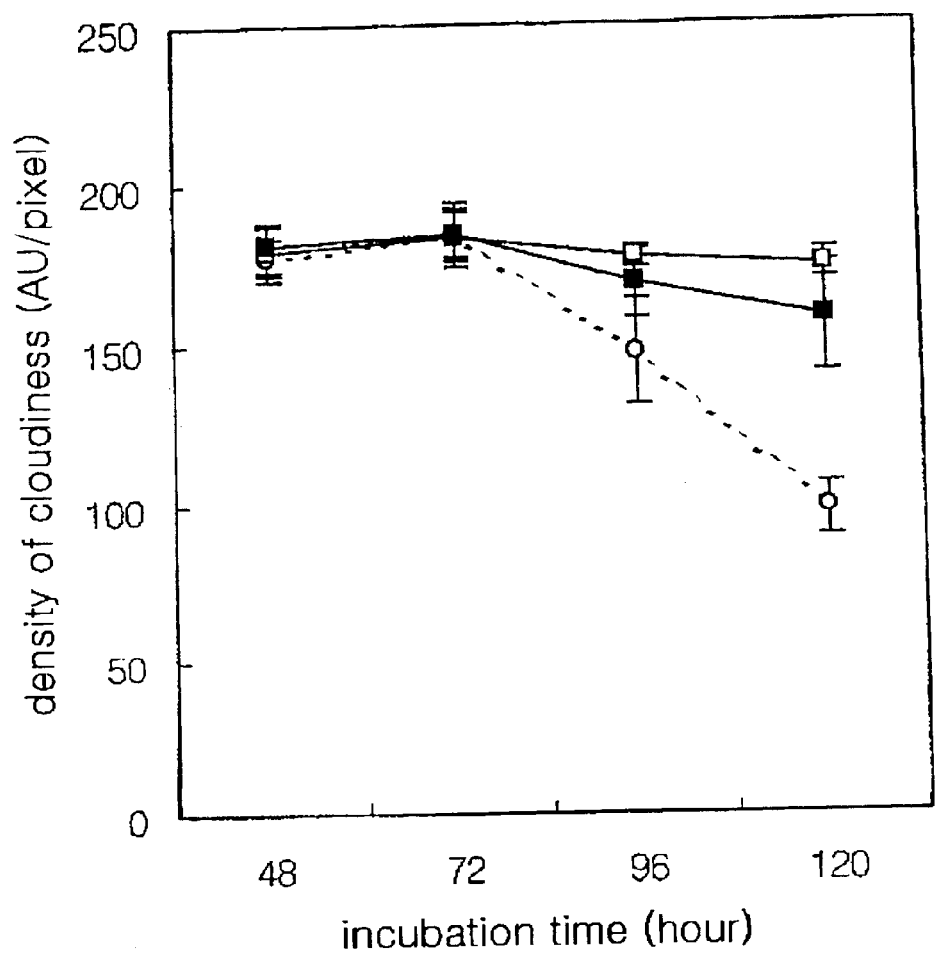

FIGS. 9 and 10 show the effects of the additional myo-inositol and taurine on the degree of cloudiness of lenses. The lenses were cultured for 24 hours in 20 mM xylose culture media. After the lenses became cloudy, 2.5 mM myo-inositol and taurine were added to 1 mg/ml of the AC fraction upon administration. FIG. 9 shows the data obtained from the experiment, of which 24 hour-incubation in xylose containing media was prior to the treatment of the additional myo-inositol and taurine as well as the AC fraction. The opacities of the lenses were reversed by M199 control media(—0—), AC-treated xylose media(—□—) and AC-treated xylose media together with myo-inositol and taurine(—■—). Values are based on three or more experiments with 4-5 lenses and expressed as the mean±S.D. As a result, the addition of myo-inositol and taurine further significantly lowered the cloudiness of lenses on the first and second day as compared to the treatment with AC fraction. However, on the third day of recovery, the degree of cloudiness in lenses with additional treatment was similar to that with AC fraction. FIG. 10 shows the effects on the cloudy lenses induced by incubation for 48 hours. The opacities of the lenses were reversed by M199 control media(—0—), AC-treated xylose media(—□—), and AC-treated xylose media together with myo-inositol and taurine(—■—). Values are based on three or more experiments with 4–5 lenses and expressed as the mean±S.D. When the induction of cataract with xylose lasted for 48 hours, the therapeutic effect of myo-inositol and taurine revealed on the second and third day. Consequently, the addition of myo-inositol and taurine expedited the reduction of cloudiness.

EXAMPLE 9

Toxicity Test of Chloroform Extract of Aralia According to the Present Invention In order to certify that the chloroform extract is safe when used as a galenical or a nutraceutical, $LD_{50}$ (a fatal dose that can kill 50% of test animals), which is an index used to indicate acute toxicity of test materials, was obtained in the following manner.

36 normal ICR mice (male, 22±1 g) were classified into Groups A to F. Each group included 6 mice. Saline was administered to Group A for the camparison. For Group B, 1,000 mg of Aralia extracts of the invention prepared in Example 1 were administered per 1 kg of body weight. 2,000 mg for Group C, 3,000 mg for Group D, 4,000 mg for Group E, and 5,000 mg for Group F were administered. $LD_{50}$ value of extracts prepared according to the present invention was measured by the Behrens-Karber method. (Takaki Keigiro et al., DRUG TEST, Minamiyamadou, Japan, p 131, 1960) An autopsy and a pathohistological test on the experimental animals were performed as follows. The results are shown in Table 2.

TABLE 2

Fatal Dose ($LD_{50}$) of Chloroform Extract of Aralia upon Oral Administration

| Test Group | Dose (mg/kg) | p.o. Number of dead animals/Number of used animals | *Z | **d |
|---|---|---|---|---|
| A | saline | 0/6 | — | — |
| B | 1,000 | 0/6 | — | — |
| C | 2,000 | 0/6 | 0 | 1,000 |
| D | 3,000 | 0/6 | 0 | 1,000 |
| E | 4,000 | 0/6 | 0 | 1,000 |
| F | 5,000 | 0/6 | 0 | 1,000 |

*Z is ½ the value of number of dead animals in two continuous doses.
**d is the difference between two continuous doses.

When the tests were terminated, the surviving mice were anesthetized with ether and then bled to death. Organs were removed from the dead mice and were examined with the naked eye for the evaluation of any abnormalities. For pathohistological examination, all examined organs were fixed in a 10% neutral formalin solution for 10 or more days and were then dehydrated. After dehydration, the organs were embedded in a paraffin embedding device (Fisher, Histomatic Tissue Processor, 166A) and then were divided into 5 $\mu$m segments by using an AO Rotary Microtome. The segments were examined after dying with hematoxylin and eosine.

Upon administration to the extent of 5000 mg of extracts prepared according to the present invention per 1 kg of mouse weight, no abnormalities were found in the liver tissue and kidney. No abnormalities were found from the histological test of the organs, such as the cardiac muscle, the stomach, the intestine, the pancreas, the lungs, the spleen, the adrenal gland, the brain, the testis, the ovaries, the bone marrow, etc.

As shown in Table 2, the chloroform extract prepared according to the present invention does not result in any acute toxic effects on all the organs, even when the allowable maximum dose of 5,000 mg per kg body weight was administered. Therefore, it is concluded that the extract is a safe material that does not cause any toxicity, such as tissue damage.

EXAMPLE 10

Characteristics of Extracts of the Present Invention According to HPLC Analysis

Figure 11:
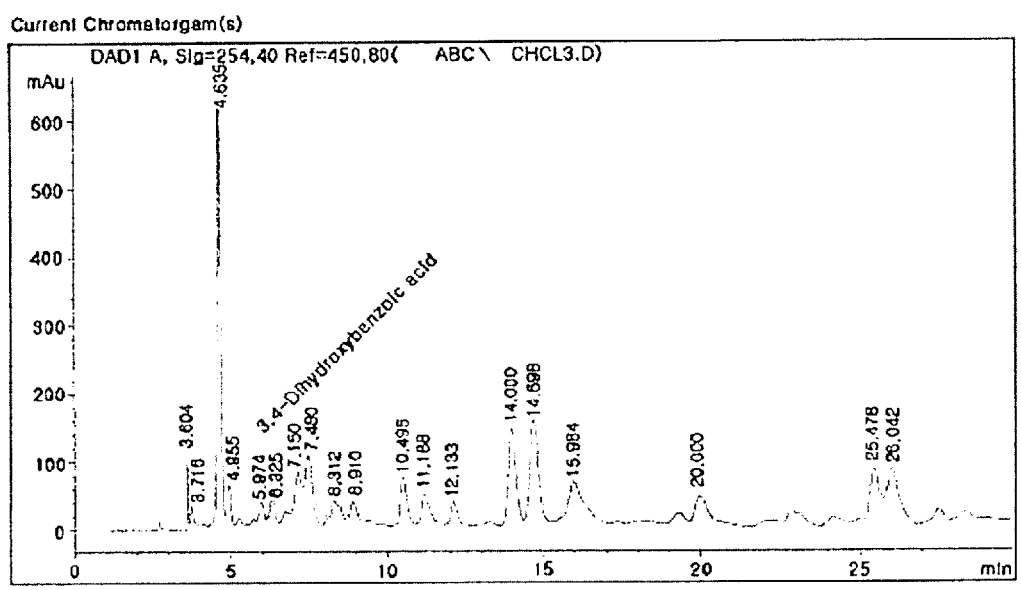
FIG. 11 is an HPLC profile of a chloroform extract of Aralia.

The chloroform extract of Aralia in the present invention was dissolved in methanol at the concentration of 10 mg/ml for HPLC analysis. 10 μl of dissolved extracts were analyzed using HPLC (HP1090) under the conditions described below. As a result of TLC that was performed on the chloroform extract of Aralia, it was found that a material that is similar to ferulic acid was contained. FIG. 11 shows an HPLC profile of the chloroform extract of Aralia. Through repeated tests, characteristic peaks of the extract were observed. 0.04% of ferulic acid (RT=25.53) was included in the chloroform fraction.

| Conditions for analysis | |
|---|---|
| Column: | μ bondapak $C_{18}$ (3.9 × 300 mm) |
| Mobile phase: | ACN/$H_2O$ (15:85) ---> ACN/$H_2O$ (80:20) (70 min) |
| Flow rate: | 1 ml/min |
| Detection: | Measurement with photodioid array detector at 254 nm |

Figure 12:
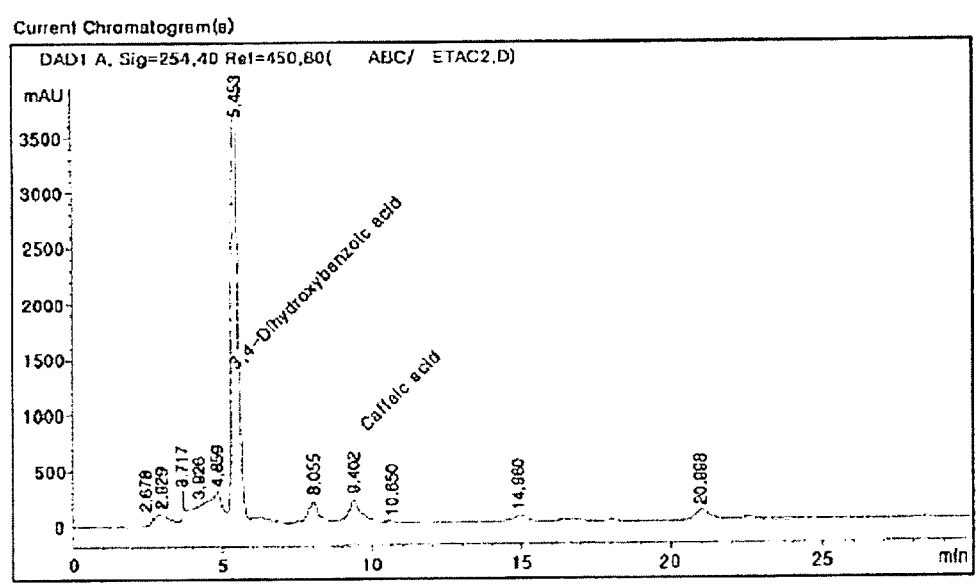
FIG. 12 is an HPLC profile of an ethyl acetate extract of Aralia.

FIG. 12 is an HPLC profile of the ethyl acetate extract of Aralia. As a result of the analysis performed under the following conditions, it was found that a substantial amount of phenolic compounds was contained. Especially, 3,4-dihydroxybenzoic acid (retention time: RT=10.941 min) was higher than other phenolic compounds content. The amount of 16.44% was contained in the ethyl acetate extract. The content of caffeic acid (RT=18.824 min) was 1.21%.

| HPLC conditions | |
|---|---|
| Mobile phase: | ACN/$H_2O$ (15:85) ---> ACN/$H_2O$ (80:20) (70 min) |
| Column: | μ bondapak $C_{18}$ (3.9 × 300 mm)/40° C. |
| Detection: | UV, Vis 254, 366 nm |
| Flow rate: | 1 ml/min |

TABLE 3

Contents of Phenolic compounds in Ethyl acetate Extract of Aralia

| | 3,4-DHBA | | Caffeic acid | |
|---|---|---|---|---|
| | RT | % | RT | % |
| Ethyl acetate Extract of Aralia | 5.453 | 16.44 | 9.402 | 1.21 |

Figure 13:
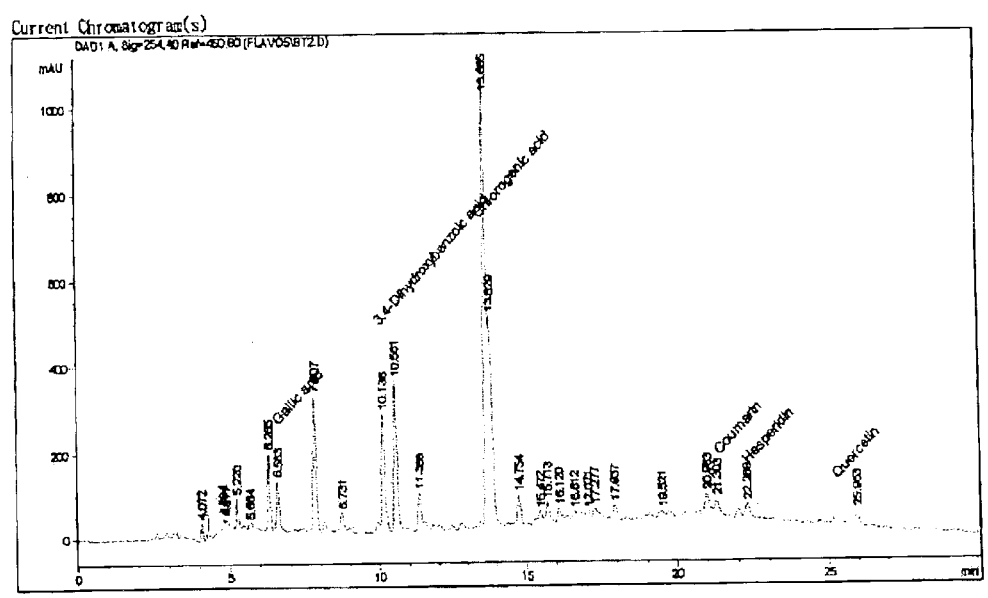
FIG. 13 is an HPLC profile of a butanol extract of Aralia.

FIG. 13 is an HPLC profile of the butanol extract of Aralia. As a result of the analysis performed under the following conditions, it was found that phenolic compounds and flavonoids were contained. As shown in Table 4, phenolic compounds, such as 3,4-dihydroxy benzoic acid, gallic acid, chlorogenic acid, coumarin, etc., and flavonoids, such as quercetin, hesperidin, etc., were contained. The content of chlorogenic acid amounting to 1.78% was the highest. In addition to chlorogenic acid beng contained in the butanol extract of Aralia, flavonoids, such as quercetin or hesperidin, have been known as having excellent anti-oxidation properties. These materials contained in the Aralia extract will be helpful in inhibiting the generation of cataract due to oxidative stress.

| Conditions for HPLC analysis are as follows: | |
|---|---|
| Mobile phase: | 2% acetic acid:MeOH = 10:0 ---> 2:8 (30 min) |
| Column: | μ bondapak $C_{18}$ (3.9 × 300 mm)/40° C. |
| Detection: | UV, Vis 254, 366 nm |
| Flow rate: | 1 ml/min |

TABLE 4

Contents of Compounds Contained in Butanol Extract of Aralia

| | Gallic acid | | 3,4-DHBA | | Chlorogenic acid | | Coumarin | | Hesperidin | | Quercetin | |
|---|---|---|---|---|---|---|---|---|---|---|---|---|
| | RT | % | RT | % | RT | % | RT | % | RT | % | RT | % |
| Butanol Extract of Aralia | 6.58 | 0.44 | 10.14 | 0.17 | 13.69 | 1.78 | 21.30 | 0.06 | 22.29 | 0.15 | 25.96 | 0.07 |

As seen above, Aralia extracts prepared according to the present invention are effective in preventing cataract induced by blood glucose, delaying the development of cataract, as well as facilitating the treatment of and recovery from cataract. In addition, myo-inositol and taurine, which are added in order to supplement the limiting components in the diabetic lenses, brings a synergism in treating cataract.

While the present invention has been described and illustrated herein with reference to the preferred embodiments thereof, it will be understood by those skilled in the art that various changes in form and details may be made therein without departing from the spirit and scope of the invention.

What is claimed is:

1. A composition comprising effective amounts of extracts of Aralia and at least one selected from the group consisting of myo-inositol and taurine, wherein said extracts of Aralia are prepared by a solvent selected from the group consisting of ethanol, methanol and a mixture thereof.

2. The composition according to claim 1, wherein said composition further comprises a pharmaceutically acceptable carrier, excipient or diluent.

3. The composition according to claim 1, wherein said composition is in an unit dosage form selected from the group consisting of a tablet, a capsule, a solution, a suspension, a syrup, a beverage, an oral or ophthalmic formulation and an injection.

4. The composition according to claim 1, wherein said composition is a beverage, a galenical or a nutraceutical formulation.

5. A composition comprising effective amounts of a chloroform fraction of Aralia and at least one selected from the group consisting of myo-inosltol and taurine, wherein said chloroform fraction of Aralia is prepared by extracting Aralia with a solvent selected from the group consisting of ethanol, methanol and a mixture thereof, and subsequently performing a second extraction on the Aralia extract with chloroform to obtain a chloroform fraction of Aralia.

6. A method for treatment of cataracts, comprising the step of administering an effective amount of a composition comprising extracts of Aralia and at least one selected from the group consisting of myo-inositol and taurine, wherein said extracts of Aralia are extracted by a solvent selected from the group consisting of ethanol, methanol and a mixture thereof.

7. The method for treatment of cataract according to claim 6, wherein said composition further comprises a pharmaceutically acceptable carrier, excipient or diluent.

8. The method for treatment of cataracts according to claim 7, wherein said composition is in an unit dosage form selected from the group consisting of a tablet, a capsule, a solution, a suspension, a syrup, a beverage, an oral or ophthalmic formulation and an injection.

9. The method for treatment of cataracts according to claim 6, wherein said composition is a beverage, a galenical or a nutraceutical formulation.

10. The method for treatment of cataracts according to claim 6, wherein said composition further comprises myo-inositol.

11. The method for treatment of cataracts according to claim 6, wherein said composition further comprises taurine.

12. The method for treatment of cataract according to claim 6, wherein said extracts of Aralia are the chloroform fraction of Aralia extracts extracted by solvent selected from the group consisting of ethanol, methanol and a mixture thereof.

* * * * *